United States Patent [19]

Joly et al.

[11] Patent Number: 5,489,730
[45] Date of Patent: Feb. 6, 1996

[54] CATALYST FOR ALKYLATION OF $C_4$–$C_5$ ISOPARAFFIN BY AT LEAST ONE $C_3$–$C_6$ OLEFIN

[75] Inventors: Jean Francois Joly, Paris; Christian Marcilly, Houilles; Eric Benazzi, Montesson; Frederic Chaigne, Bauvoir S/Mer; Jean Yves Bernhard, Mennecy, all of France

[73] Assignee: Institut Francais du Petrole, Rueil Malmaison, France

[21] Appl. No.: 304,186

[22] Filed: Sep. 12, 1994

[30] Foreign Application Priority Data

Sep. 10, 1993 [FR] France ................................ 93 10896
Dec. 14, 1993 [FR] France ................................ 93 14994

[51] Int. Cl.$^6$ .................................................. C07C 2/62
[52] U.S. Cl. ...................... 585/731; 502/202; 502/216; 585/724; 585/730
[58] Field of Search .............................. 585/730, 731, 585/726; 502/202, 216

[56] References Cited

U.S. PATENT DOCUMENTS 4,950,139  8/1990  Fennemann et al. .
5,336,833  8/1994  Joly et al. ................................ 585/731

FOREIGN PATENT DOCUMENTS 2081271   4/1993   Canada .
67467     5/1982   European Pat. Off. .
325811   12/1988   European Pat. Off. .
539277   10/1992   European Pat. Off. .
2682891   4/1993   France ................................ 585/731
2683739   6/1993   France ................................ 585/731

OTHER PUBLICATIONS

Aldrich Catalog, pp. 1250–1251.

Primary Examiner—Asok Pal
Attorney, Agent, or Firm—Millen, White, Zelano & Branigan

[57] ABSTRACT

The present invention relates to a catalyst comprising silica and sulphuric acid which impregnates said silica, and the use of said catalyst in catalytic alkylation of isobutane and/or isopentane in the presence of at least one olefin containing 3 to 6 carbon atoms per molecule, said catalyst being characterized in that the silica, prior to its impregnation with sulphuric acid, has a total porous volume greater than 1.5 $cm^3$ per gram and in that said catalyst consists essentially of particles of an average diameter of between 0.1 and 150 μm.

14 Claims, No Drawings

CATALYST FOR ALKYLATION OF $C_4$–$C_5$ ISOPARAFFIN BY AT LEAST ONE $C_3$–$C_6$ OLEFIN

BACKGROUND OF THE INVENTION

The present invention relates to a catalyst comprising silica and an acid phase containing sulphuric acid and its use in catalytic alkylation of isobutane and/or isopentane by at least one olefin, which allows at least one product, for example dimethylbutanes, trimethylpentanes, trimethylhexanes and trimethylheptanes, to be obtained.

It is known that in order to supply internal combustion engines with spark ignition, and particularly engines with a high compression ratio, it is particularly advantageous to have fuels with high octane ratings, that is to say consisting essentially of heavily branched paraffin hydrocarbons. The alkylation of at least one isoparaffin (isobutane and/or isopentane) by at least one olefin containing 3 to 6 carbon atoms per molecule allows such products to be obtained. This reaction requires the use of very acidic catalysts, particularly for reducing parasitic reactions such as hydride abstraction from the olefin and of polymerization which provide slightly branched hydrocarbons with a low octane rating and unsaturated hydrocarbons, cracking reactions and dismutation reactions.

The existing processes for production of hydrocarbons by alkylation of isobutane by olefins generally use either sulphuric acid or hydrofluoric acid as the catalyst. In these processes the acid catalyst constitutes a liquid phase which is placed in contact with the liquid isobutane/olefin(s) mixture to form an emulsion. These processes are expensive and give rise to significant problems with regard to personal and environmental safety. In order to remedy these problems, different catalytic systems of sulphuric acid and hydrofluoric acid in liquid phase have been sought.

European patent application EP-A-0 539 277 describes a catalyst containing silica and a solid acid phase comprising sulphuric acid, the silica according to said patent application is such that its porous volume is between 0.005 and 1.5 $cm^3$ per gram and its specific surface is between 0.01 and 1,500 $m^2$ per gram. Said acid phase can if required contain an additive selected from the group formed by $H_3PO_4$, $B(OH)_3$, $BF_4H$, $FSO_3H$, $CF_3CO_2H$, $SbF_5$, $CF_3SO_3H$ and $SO_3$.

European patent applications EP-A-0542612 and EP-A-0542620 describe the same type of catalyst, but with different supports: the catalyst support described in EP-A-0542612 contains at least one sulphated oxide and the catalyst support described in EP-A-0542620 is selected from among resins, carbon, zeolites, and oxides such as $ZrO_2$, $T_2O_2$, $Al_2O_3$, $Fe_2O_3$, $HfO_2$ and used cracking catalysts.

SUMMARY OF THE INVENTION

The present invention relates to a catalyst for the alkylation of at least one isoparaffin (isobutane and/or isopentane) with at least one clefin containing 3 to 6 carbon atoms per molecule. More precisely, the invention relates to a catalyst comprising silica and an acid phase containing sulphuric acid, the silica having been impregnated with said acid phase, its preparation and use in catalytic alkylation of isobutane and/or isopentane in the presence of at least one clefin containing 3 to 6 carbon atoms per molecule, said catalyst being characterised in that it consists essentially of particles with an average diameter of between 0.1 and 150 μm (1 μm=$10^{-6}$ m), preferably between 5 and 110 μm and even more preferably between 5 and 80 μm and in that the silica, before its impregnation with said acid phase, has a total porous volume greater than 1.5 $cm^3$ per gram, preferably between 1.5 and 6 $cm^3$ per gram.

The catalyst according to the present invention leads to improved catalytic performance with respect to those described in European patent application EP-A-0539277.

The catalyst according to the invention is such that its content by weight of acid phase is generally greater than 70%.

The silica can possibly contain impurities such as, for example, oxides, alkalines, alkaline-earths, aluminium compounds or any other impurities known to the man skilled in the art, the total quantity of the impurities generally not exceeding 2% by weight of the silica.

The titre of the sulphuric acid is advantageously between 90 and 100% by weight, preferably between 97 and 100% by weight, and even more preferably between 98 and 100% by weight.

It is possible to add at least one additive to said acid phase containing sulphuric acid before impregnation to improve the catalytic performance.

The additive is generally selected from the group formed by $H_3PO_4$, $B(OH)_3$, $HB(HSO_3)_4$, $BF_4H$, $FSO_3H$, $CF_3CO_2H$, $SbF_5$, $CF_3SO_3H$ and $SO_3$; the additive is preferably trifluoromethane sulphonic acid $CF_3SO_3H$ or sulphuric anhydride $SO_3$, but any additive known to the man skilled in the art is conceivable.

The total additive(s) content of the acid phase depends upon numerous parameters, among which the nature of the additive can be mentioned. For example, when the additive used is trifluoromethane sulphonic acid $CF_3SO_3H$, the total content of additive in the acid phase is generally between 0.1 and 50% by weight, preferably between 0.1 and 30% by weight, and even more preferably between 5 and 15% by weight.

The acid phase occupies between 80 and 100% of the total porous volume of the silica, preferably between 90 and 100% of said porous volume.

The silica is generally such that, before its impregnation with the acid phase, its specific surface is between 0.1 and 1,500 $m^2$ per gram. Moreover, it is generally constituted of particles of an average diameter of between 0.1 and 150 μm.

The process for preparation of the catalyst according to the invention comprises two stages. In a first stage the silica is calcined at a temperature greater than 50° C., preferably greater than 80° C. and even more preferably between 150° and 600° C., for example equal to approximately 500° C. The duration of this calcination stage is normally between 10 minutes and 50 hours, preferably between 15 minutes and 25 hours. The calcination is generally carried out in the presence of dry air or a dry air/nitrogen mixture, at a rate of between 0.001 and 10 liters per hour per gram, preferably between 0.1 and 5 l/h/g. The second stage involves impregnation of said calcined silica with said acid phase. Any of the techniques well known to the man skilled in the art can be used to carry out this stage. A stage of preparation of the acid phase, prior to the impregnation stage can be added to this process of preparation.

The catalyst according to the invention thus prepared has not been subjected to any calcination subsequent to the impregnation stage. When it is used in the alkylation of isoparaffin(s) by at least one olefin, it is not subjected, prior to its use, to any calcination and thus between the impregnation stage and said use, it is not subjected to any calcination. The catalyst according to the invention thus prepared is therefore immediately ready for use. The catalyst according to the present invention is used in a process which allows the alkylation reaction of isoparaffin by at least one olefin to be carried out in the best conditions. in particular said reaction being characterised by strong exothermic reaction (approximately 83.6 kJ per mol of transformed butene), the process in which the catalyst according to the present invention is used allows a good temperature homogeneity and concentration of reactants to be obtained.

In the process of alkylation of isoparaffin using the catalyst according the present invention, the operating conditions, and more particularly the temperature and pressure, are generally selected in a manner such that the mixture constituted by the isoparaffin(s), the olefin(s) and the reaction products is liquid. Moreover, it is important that the catalyst is immersed in said liquid in order to ensure that there is a good liquid/solid contact everywhere.

The catalyst according to the invention is advantageously used in the reaction zone of alkylation of isobutane and/or isopentane with at least one olefin comprising 3 to 6 carbon atoms per molecule, in a liquid phase and in a mixture together with isoparaffin or a mixture of isoparaffins. The catalyst according to the invention can be used in an expanded bed, in an almost perfectly agitated reaction zone, or circulating bed, and is preferably used in a process which uses a continuous liquid phase, the catalyst being used in the form of a suspension, for example, according to the two implementations described hereinafter.

In the case where the catalyst is used in the form of a suspension, in a first implementation a reaction zone with an almost pedect mix can be used, that is to say with a perfect mix or near-perfect (agitated or Grignard vessel), using at least one agitation means, for example by means of a helix, in order to obtain sufficient agitation of the catalyst in suspension in the hydrocarbonated liquid phase, which consists generally of isoparaffin(s) (isobutane and/or isopentane), at least one olefin, possibly at least one inert dilutant (for example, propane and normal butane) and the products of the alkylation reaction. The charge to be converted, composed of isobutane and/or isopentane and at least one olefin can be, for example, introduced in a liquid form at at least one point within the hydrocarbonated liquid phase present in the reaction zone.

A second implementation of the catalyst according to the present invention in suspension in a hydrocarbonated phase is the cocurrent flow fluidized bed or circulating bed. In this implementation the catalyst in suspension in the hydrocarbonated liquid phase, generally containing isobutane and/or isopentane, at least one olefin, possibly at least one inert diluent (for example propane or normal butane) and the products of the alkylation reaction, circulate from bottom to top in the reaction zone. The group constituted by the suspension of the catalyst in the hydrocarbonated phase then circulates through at least one heat exchanger and at least one pump, before being introduced again at the entrance to the reaction zone. The charge to be converted, constituted by isobutane and/or isopentane and at least one olefin is introduced either in liquid form or in gaseous form at at least one point in the reaction zone.

In the two types of implementation previously described, isoparaffin (isobutane and/or isopentane) not having been convened, or having been introduced in excess with respect to the stoichiometry of the reaction, is generally recycled after separation of the alkylate, either by direct introduction into the reaction zone or by mixing with the charge to be convened.

The isoparaffin(s)/olefin(s) mixture is generally introduced into the reaction zone at a spatial speed per hour, expressed in weight of olefin introduced per unit of catalyst and per hour (w.p.h.) of between 0.001 and $10h^{-1}$, and preferably between 0.002 and $2h^{-1}$. Said mixture can also be produced in the interior of the reaction zone. On all cases, the mixture constituted in this manner is in the reaction zone under conditions of pressure and temperature such that the mixture of hydrocarbons remains liquid on the catalyst.

The reaction temperature is generally lower than +10° C., preferably lower than 0° C. and in manner often more preferable, lower than −3° C. The pressure of the reaction zone is sufficient to maintain the hydrocarbons in a liquid state in said zone.

In order to limit secondary reactions, an excess of isoparaffin(s) with respect to the olefin(s) can be used. By way of example, in the case of alkylation of isobutane by a butene, the isobutane can be introduced pure in the charge or in the form of a mixture of butanes containing, for example, at least 40% isobutane. Moreover, a pure butane or else a mixture of isomeric butanes can be introduced. In any case, the isobutane/butene(s) molar ratio in the charge is generally between 1 and 100, preferably between 3 and 50 and in a manner often preferred, between 5 and 15.

When the nature of the catalyst and the reaction conditions and chosen judiciously (in particular the temperature), the catalyst according to the invention allows the production of alkylation products of at least one isoparaffin by at least one clefin which are valuable as fuels for engines and constituents for petrol, and which consist of, for example, at least 60% mols of paraffin having 8 atoms of carbon per molecule and less than 1% mols of non-saturated compounds, the paraffins consisting of 8 atoms of carbon per molecule composed of 70 to 98% in mols of trimethylpentanes.

Another advantage of the catalyst according to the present invention is the possibility of alkylising isoparaffin with mixtures of clefins with 3 to 6 carbon atoms per molecule at low temperatures, where the proportion of olefins with 4 atoms of carbon per molecule is very significant.

The following examples illustrate the invention without thereby limiting the scope thereof.

EXAMPLE 1

Example 1

Catalysts containins Sulphuric Acid
Preparation of the Catalyst According to the Invention 15 g of silica with a porous volume equal to 2.2 $cm^3$ per gram, with a specific surface equal to 420 $m^2$ per gram, with particles of an average diameter equal to 60 μm (1 μm=$10^{-6}$ m) is activated by drying at 150° C. for 12 hours. The silica thus activated is preserved in nitrogen. Then dry impregnation of 10 g of said calcined silica is carried out with 40.5 g of a solution of sulphuric acid at 99.8% by weight. The solid obtained, designated catalyst A, has a content by weight of sulphuric acid equal to 80.2% by weight. It is kept protected from humidity.

Preparation of Catalyst B According to Patent Application EP-A-0539277 (Comparative)

15 g of silica with a porous volume equal to 0.78 $Cm^3$ per gram, with a specific surface equal to 30 $m^2$ per gram, with particles of an average diameter equal to 65 μm is activated by drying at 150° C. for 12 hours. The silica thus activated is preserved in nitrogen. Then dry impregnation of 10 g of said calcined silica is carried out with 14.35 g of a solution of sulphuric acid at 9.8% by weight. The solid obtained, designated catalyst B, has a content by weight of sulphuric acid equal to 58.9% by weight. It is kept protected from humidity.

Preparation of Comparative Catalyst C 30 g of silica with a porous volume equal to 0.32 cm$^3$ per gram, with a specific surface equal to 250 m$^2$ per gram, with particles of an average diameter equal to 59 μm is activated by drying at 150° C. for 12 hours. The silica thus activated is preserved in nitrogen. Then dry impregnation of 26 g of said calcined silica is carried out with 14 g of a solution of sulphuric acid at a titre of 99.7% by weight. The solid obtained, designated catalyst C, has a content by weight of sulphuric acid equal to 35% by weight. It is kept protected from humidity.

Alkylation of Isobutane by Butene-1

20 g of catalyst A, B or C prepared according to the method described above is introduced into a glass reactor of the Fischer & Porter type with a volume of 360 ml, previously purged by argon discharge. The reactor containing the catalyst is then closed, then placed under low vacuum, then cooled to the temperature of −20° C.

150 cm$^3$ of isobutane is then added to the reactor containing the catalyst while agitating, said reactor being immersed in a cold bath at −5° C. The catalyst+ isobutane system is kept agitated for 30 minutes in order to homogenize the temperature.

2.6 g of butene-1 per hour is added regularly for a total of 6 hours, the temperature of the reactor being maintained at −5° C. for the whole duration of the injection.

After reaction, the hydrocarbon phase is drawn off from the reactor, then the isobutane is slowly evaporated and the alkylate is collected and analyzed by chromatography in the vapor phase. Its composition by weight is given in table 1 hereafter. The olefin conversion is 100%.

TABLE 1

| COMPOUNDS | CATALYST A according to the invention | CATALYST B comparative | CATALYST C comparative |
|---|---|---|---|
| $C_5$–$C_7$ | 3.4 | 10.1 | 13 |
| TMPs | 86.6 | 71.16 | 54.4 |
| DMHs | 6.3 | 8.44 | 8.1 |
| $C_9^+$ | 3.7 | 10.3 | 24.5 |

TMPs: trimethylpentanes
DMHs: dimethylhexanes

Thus, catalyst A according to the present invention gives better results than comparative catalyst B, but above all better results than comparative catalyst C, that is to say on the one hand the alkylate obtained by said catalyst A contains more trimethylpentanes than the alkylate obtained by catalysts B and C, and on the other hand the quantity of heavy products obtained by the use of catalyst A is less than in the case of use of catalysts B or C.

Example 2

Catalysts containing Sulphuric Acid and Trifluoromethane Sulphonic Acid
Comparative Catalyst: Catalyst D 16 g of silica with a specific surface equal to 40 m$^2$ per gram, with a porous volume equal to 1.2 cm$^3$ per gram, and principally constituted of substantially spherical grains of an average diameter equal to 110 μm is activated by calcination in air for 4 hours at 500° C. The silica thus activated is preserved in argon. Then dry impregnation, protected from humidity, of 14 g of said dehydrated silica is carried out with 22 g of the mixture composed of:

18.7 g of a solution containing 99% by weight of $H_2SO_4$ and 1% by weight of water, 3.3 g of a solution containing 97.8% of $CF_3SO_3H$ and 2.2% by weight of water.

The composition by weight of the acid phase is as follows:

$H_2SO_4$: 84.15%

$CF_3SO_3H$: 14.68%

$H_2O$: 1.17%

The solid thus obtained, catalyst D, contains therefore 61% by weight of acid phase. It is preserved in argon at −18° C.

Catalyst According to the Invention: Catalyst E 16 g of macroporous silica with a specific sudace equal to 435 m$^2$ per gram, with a porous volume equal to 2.5 cm$^3$ per gram, and principally constituted of substantially spherical grains of an average diameter equal to 70 μm is activated by calcination in air for 4 hours at 500° C. The silica thus activated is preserved in argon. Then dry impregnation, protected from humidity, of 14 g of said dehydrated silica is carried out with 63.4 g of the mixture composed of:

53.89 g of a solution containing 99% by weight of $H_2SO_4$ and 1% by weight of water, 9.51 g of a solution containing 97.8% of $CF_3SO_3H$ and 2.2% by weight of water.

The composition by weight of the acid phase is as follows:

$H_2SO_4$: 84.15%

$CF_3SO_3H$: 14.68%

$H_2O$: 1.17%

The solid thus obtained, catalyst E, contains therefore 81.9% by weight of acid phase. It is preserved in argon at −18° C.

Results of Tests for Alkylation of Isobutane by Butene-1

Catalysts D and E are used to alkylate isobutane by butene-1 such as to produce branched paraffins with octane ratings. The catalysts D and E are tested according to the same operating protocol as described hereafter.

36 g of the catalyst D or E is introduced into a glass reactor of the Fischer & Porter type with a volume of 360 ml, previously purged by argon discharge. The reactor containing the catalyst is then closed, then placed under low vacuum, then cooled to the temperature of −20° C.

100 cm$^3$ of isobutane is then added to the reactor containing the catalyst while agitating, said reactor being immersed in a cold bath at −6° C. The catalyst+ isobutane system is kept agitated for 30 minutes in order to homogenize the temperature.

A mixture of isobutane and butene-1, containing 20% by weight of butene-1 is added continuously for a total of 8 hours, the temperature of the reactor being maintained at −5° C. for the whole duration of the injection. The volume supply of butene-1 is equal to 10 ml per hour.

After reaction, the hydrocarbon phase is drawn off from the reactor, then the isobutane is slowly evaporated and the alkylate is collected and analyzed by chromatography in the vapor phase. Its composition by weight is given in table 2 hereafter. The olefin conversion is 100%.

TABLE 2

|  | CATALYST D (comparative) | CATALYST E (according to the invention) |
|---|---|---|
| $C_5$–$C_7$ | 2.5 | 1.8 |
| total $C_8$ | 93 | 95.1 |
| $C_9^+$ | 4.5 | 3.1 |
| TMPs/$C_8$ | 94 | 94.1 |

TMPs/$C_8$: proportion of trimethylpentanes (224, 223, 234 and 233 isomers) in the $C_8$ fraction.

Example 3

Catalysts containing Sulphuric Acid and Sulphuric Anhydride

Preparation of Catalyst F (comparative)

14 g of macroporous silica with a specific surface equal to 27 m² per gram, with a porous volume equal to 1 cm³ per gram, and principally constituted of substantially spherical grains of an average diameter equal to 42 µm is activated by calcination in air for 4 hours at 500° C. The solid thus activated is preserved in argon. Then dry impregnation of 10 g of said calcined solid is carried out with 7 cm³ of the mixture composed of 80% by weight of sulphuric acid (100% titre) and 20% by weight of sulphuric arthydride. The catalyst thus obtained, catalyst F, contains 13.5 g of oleum and 10 g of silica, that is 57.4% by weight of acid phase, and is preserved in an argon atmosphere at −18° C.

Preparation of Catalyst G (according to the invention)

14 g of macroporous silica with a specific surface equal to 456 m² per gram, with a porous volume equal to 2.1 cm³ per gram, and principally constituted of substantially spherical grains of an average diameter equal to 42 µm is activated by calcination in air for 4 hours at 500° C. The solid thus activated is preserved in argon. Then dry impregnation of 10 g of said calcined solid is carried out with 20 cm³ of the mixture composed of 80% by weight of sulphuric acid (100% titre) and 20% by weight of sulphuric anhydride. The catalyst thus obtained, catalyst G, contains 38.57 g of oleum and 10 g of silica, that is 79.4% by weight of acid phase, and is preserved in an argon atmosphere at −18° C.

Alkylation of Isobutane by Butene-1

20 g of the catalyst F is introduced into a glass reactor of the Fischer & Porter type with a volume of 360 ml, previously purged by argon discharge. The reactor containing the catalyst is then closed, then placed under low vacuum, then cooled to the temperature of −20° C.

72 cm³ of isobutane is then added to the reactor containing the catalyst while agitating, said reactor being immersed in a cold bath at −20° C. The catalyst +isobutane system is kept agitated for 30 minutes in order to homogenize the temperature.

135 cm³ of a mixture of 24% by weight of butene-1 and 76% by volume of isobutane is added regularly for a total of 10 hours, the temperature of the reactor being maintained at −15° C. for the whole duration of the injection.

After reaction, the hydrocarbon phase is drawn off from the reactor, then the isobutane is slowly evaporated and the alkylate is collected and analyzed by chromatography in the vapor phase. its composition by weight is given in table 3 hereafter.

TABLE 3

|  | CATALYST F (comparative) | CATALYST G (according to the invention) |
|---|---|---|
| $iC_5$ | 1.1 | 1.1 |
| $C_6$ | 1.3 | 0.8 |
| $C_7$ | 2.1 | 1.4 |
| $C_8$ | 88.1 | 92.8 |
| $C_9$ | 1.6 | 0.8 |
| $C_9^+$ | 5.3 | 3.1 |

With catalyst F, the conversion of the olefin is 98%, the alkylation yield 200% with respect to the transformed olefin, and the Ca fraction contains 88.6% by weight of trimethylpentanes (224, 223, 234 and 233 isomers in the $C_8$ fraction).

With catalyst G, the conversion of the olefin for catalyst G is 100%, the alkylation yield 200% with respect to the transformed olefin, and the $C_8$ fraction contains 91.8% of trimethylpentanes (223, 223, 234 and 233 isomers in the $C_8$ fraction).

We claim:

1. A catalyst containing silica and an acid phase comprising sulphuric acid, the silica having been impregnated with said acid phase and said catalyst consisting of particles with an average diameter of 0.1 to 150µm, wherein the silica, prior to its impregnation with said acid phase, has a total porous volume of greater than 1.5 cm³ per gram.

2. A catalyst according to claim 1, wherein its content by weight of acid phase is greater than 70%.

3. A catalyst according to claim 1, wherein the silica has, prior to its impregnation with said acid phase, a total porous volume of between 1.5 and 6 cm³ per gram.

4. A catalyst according to claim 1, wherein said acid phase further contains at least one additive which is $H_3PO_4$, $B(OH)_3$, $HB(HSO_3)_4$, $BF_4H$, $FSO_3H$, $CF_3CO_2H$, $SbF_5$, $CF_3SO_3H$ and $SO_3$.

5. A catalyst according to claim 1, wherein said additive is trifluoromethane sulphonic acid $CF_3SO_3H$.

6. A catalyst according to claim 1, wherein said additive is sulphuric anhydride.

7. A process for the preparation of a catalyst according to claim 1, comprising calcining the silica at a temperature greater than 50° C., and impregnating the silica with an acid phase containing sulphuric acid in a concentration of 90 to 100% by weight.

8. A process of catalytic alkylation of at least one isoparaffin by at least one olefin containing 3 to 6 carbon atoms per molecule, said process comprising subjecting said isoparaffin and olefin to alkylation conditions in the presence of a catalyst of claim 1, in which process the reaction temperature is lower than 10° C. and the pressure of the reaction zone is sufficient to maintain the hydrocarbons in liquid state in said zone.

9. A process to claim 8 in which the catalyst is used in a perfect or near-perfect mixture reaction zone.

10. A process to claim 8 in which the catalyst is used in a cocurrent flow fluidized bed.

11. A catalyst according to claim 1, wherein the isoparaffin is at least one of isobutane or isopentane.

12. A catalyst according to claim 1, wherein the silica has, prior to its impregnation with said acid phase, a total porous volume of greater than 2 cm³ per gram.

13. A catalyst according to claim 1, wherein the silica has, prior to its impregnation with said acid phase, a total porous volume of 2.1 to 6 cm³ per gram.

14. A catalyst according to claim 1, wherein the silica has, prior to its impregnation with said acid phase, a total porous volume of 2.5 to 6 cm³ per gram.

* * * * *